US010468128B2

(12) United States Patent
Davies et al.

(10) Patent No.: US 10,468,128 B2
(45) Date of Patent: Nov. 5, 2019

(54) APPARATUS AND METHOD FOR PRESENTATION OF MEDICAL DATA

(71) Applicant: Toshiba Medical Systems Corporation, Otawara-shi (JP)

(72) Inventors: Michelle Louise Davies, Edinburgh (GB); Euan Robertson, Edinburgh (GB); John Zurowski, Edinburgh (GB); Yusuke Kano, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 103 days.

(21) Appl. No.: 15/484,575

(22) Filed: Apr. 11, 2017

(65) Prior Publication Data

US 2018/0292978 A1    Oct. 11, 2018

(51) Int. Cl.
| G06F 3/048 | (2013.01) |
| G06Q 30/00 | (2012.01) |
| G06Q 50/00 | (2012.01) |
| G16H 10/60 | (2018.01) |
| G06F 3/0484 | (2013.01) |
| G16H 15/00 | (2018.01) |

(52) U.S. Cl.
CPC ......... *G16H 10/60* (2018.01); *G06F 3/04845* (2013.01); *G06F 3/04847* (2013.01); *G16H 15/00* (2018.01)

(58) Field of Classification Search
CPC . G06F 3/048; G06F 3/00; G06F 17/30; G06F 17/00; G06F 19/00; G06Q 30/00; G06Q 50/00
See application file for complete search history.

(56) References Cited

U.S. PATENT DOCUMENTS

2006/0294476 A1* 12/2006 Buckley ............... G06F 3/0482
                                                                715/781
2007/0198301 A1*  8/2007 Ayers ............... G06F 17/30554
                                                                705/3

(Continued)

FOREIGN PATENT DOCUMENTS

| JP | 2001-142988 A | 5/2001 |
| JP | 2015-197736 A | 11/2015 |
| JP | 2016-81084 A | 5/2016 |

OTHER PUBLICATIONS

Frederik Seiffert, "LastHistory, Visualizing Last.fm Listening Histories and Personal Streams" Retrieved from the Internet: http://www.frederikseiffert.de/lasthistory, Feb. 17, 2010, p. 1-2.

*Primary Examiner* — Hugo Molina
(74) *Attorney, Agent, or Firm* — Oblon, McClelland, Maier & Neustadt, L.L.P.

(57) ABSTRACT

A medical data presentation apparatus comprises processing circuitry and at least one display device, the processing circuitry configured to: obtain medical data relating to a patient or other subject; display on the at least one display device at least some of the medical data on a first presentation panel of a plurality of presentation panels; receive from a user a selection of at least one feature of the first presentation panel; and, in response to the selection of the at least one feature, highlight at least one feature on a second presentation panel of the plurality of presentation panels, the second presentation panel having a different type of data presentation than the first presentation panel.

23 Claims, 9 Drawing Sheets

(56) References Cited

U.S. PATENT DOCUMENTS

| | | | |
|---|---|---|---|
| 2011/0046974 A1* | 2/2011 | Burks | G06Q 50/22 705/2 |
| 2011/0191767 A1* | 8/2011 | Pinsky | G06F 9/445 717/176 |
| 2013/0275151 A1* | 10/2013 | Moore | G06Q 10/10 705/3 |
| 2014/0075380 A1* | 3/2014 | Milirud | G06F 11/323 715/810 |
| 2014/0297278 A1 | 10/2014 | Flanagan et al. | |
| 2015/0052496 A1* | 2/2015 | Helms | G06F 8/34 717/109 |
| 2015/0339868 A1* | 11/2015 | Okuda | G01D 7/04 701/29.1 |
| 2015/0356647 A1* | 12/2015 | Reiser | G06Q 30/04 705/3 |
| 2017/0014090 A1 | 1/2017 | Tsugo | |
| 2017/0105040 A1* | 4/2017 | Gao | H04N 21/4316 |
| 2017/0277663 A1* | 9/2017 | Reimherr | G06F 17/218 |

\* cited by examiner

APPARATUS AND METHOD FOR PRESENTATION OF MEDICAL DATA

FIELD

Embodiments describes herein relate generally to presentation of medical data, for example to an apparatus and method for visually highlighting medical data within different presentations.

BACKGROUND

The amount of data captured for a given patient by hospital systems is ever increasing. As the amount of data increases, it may become more and more challenging to present this data in an optimal way to communicate the right information at the right time to make clinical decisions.

Clinical data may be collected and stored in one format, for example as a lab report. However, it may be possible to present the same data in many different ways or formats that may be suitable for different tasks within a clinical workflow.

A clinician may have many items of discrete clinical data available for a given patient it may be assumed that the clinician has available to them different ways to display the items of clinical data. The items may be displayed within different context and/or alongside different related data, for example by using a multi-panel clinical review application.

For example, consider a record of a lab result for a patient. The record of the lab result may be presented as part of a trend graph over time; as part of a table of results; as part of a timeline of clinical events; and/or as part of a summary report for an episode of care. The record of the lab result may be referred to as part of a clinical note (for example, within a paragraph) and/or referenced as part of a medical history.

The clinician may want to easily switch between different displays that align best with one or more clinical tasks, but may want to avoid effort in re-finding a record of interest in a new context.

BRIEF DESCRIPTION OF DRAWINGS

Embodiments are now described, by way of non-limiting example, and are illustrated in the following figures, in which.

DETAILED DESCRIPTION

Certain embodiments provide a medical data presentation apparatus, comprising processing circuitry and at least one display device, the processing circuitry configured to: obtain medical data relating to a patient or other subject; display on the at least one display device at least some of the medical data on a first presentation panel of a plurality of presentation panels; receive from a user a selection of at least one feature of the first presentation panel; and, in response to the selection of the at least one feature, highlight at least one feature on a second presentation panel of the plurality of presentation panels, the second presentation panel having a different type of data presentation than the first presentation panel.

Certain embodiments provide a medical data presentation method, comprising: obtaining medical data relating to a patient or other subject; displaying at least some of the medical data on a first presentation panel of a plurality of presentation panels; receiving from a user a selection of at least one feature of the first presentation panel and, in response to the selection of the at least one feature, highlighting at least one feature on a second presentation panel of the plurality of presentation panels, the second presentation panel having a different type of data presentation than the first one of the presentation panels.

Figure 1:
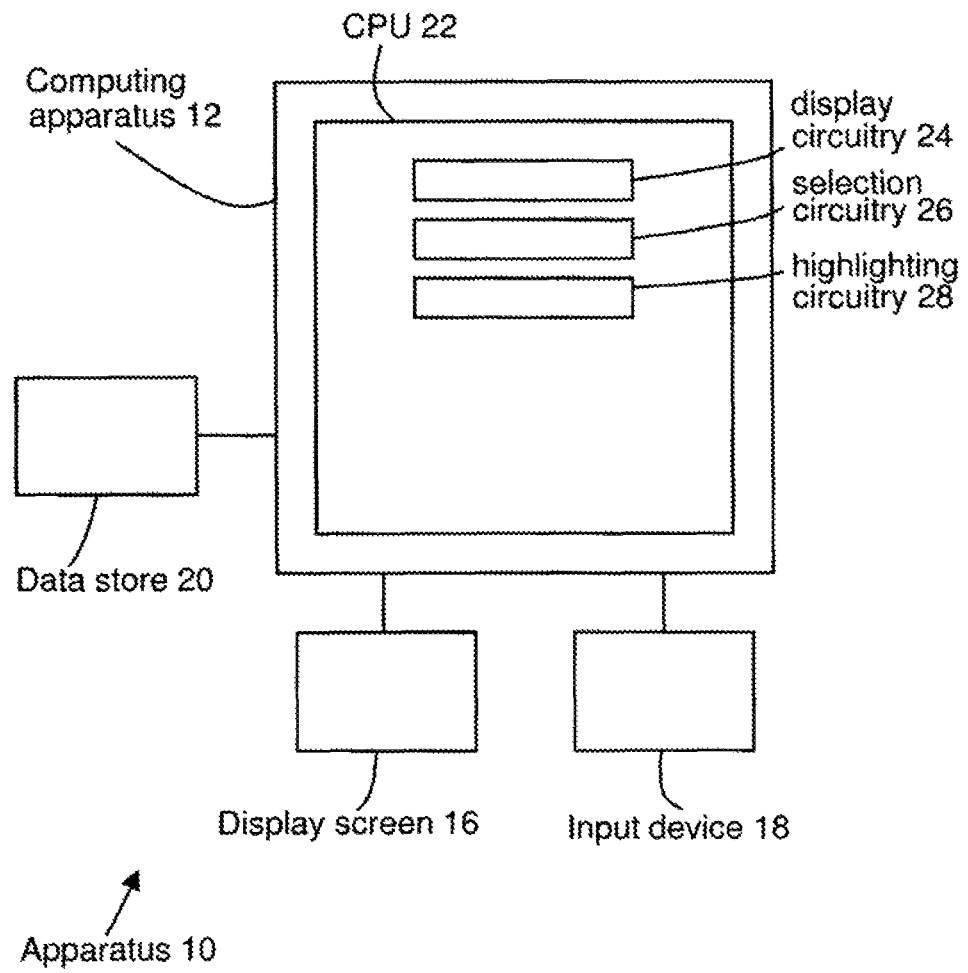
FIG. 1 is a schematic illustration of an apparatus in accordance with an embodiment.

A medical data presentation apparatus 10 according to an embodiment is illustrated schematically in FIG. 1. In the present embodiment, the medical data presentation apparatus 10 is configured to present medical data for a patient or other subject. The medical data may comprise, for example, clinical notes, lab results, and medical imaging data. In other embodiments, the medical data presentation apparatus 10 is configured to present any appropriate medical data, where medical may include veterinary.

The medical data presentation apparatus 10 comprises a computing apparatus 12, which in this case is a personal computer (PC) or workstation. The computing apparatus 12 is connected to a display screen 16 or other display device, and an input device or devices 18, such as a computer keyboard and mouse. In alternative embodiments, the display screen 16 is a touch screen, which also acts as an input device 18. In some embodiments, the computing apparatus 12 is a mobile device, for example a smartphone or tablet computer. In some embodiments, the computing apparatus 12 comprises two or more computing devices, which may be connected by a cable or wirelessly.

The computing apparatus 12 receives medical data from a data store 20. In alternative embodiments, the medical data presentation apparatus 10 receives medical data from one or more further data stores (not shown) instead of or in addition to data store 20. For example, the medical data presentation apparatus 10 may receive medical data from one or more remote data stores (not shown) which may form part of a Picture Archiving and Communication System (PACS) or other information system, for example a laboratory data archive, an Electronic Medical Record (EMR) system, or an Admission Discharge and Transfer (ADT) system.

Computing apparatus 12 provides a processing resource for automatically or semi-automatically processing medical data. Computing apparatus 12 comprises a central processing unit (CPU) 22.

Computing apparatus 12 includes display circuitry 24 configured to display medical data on a plurality of presentation panels on display screen 16; selection circuitry 26 configured to receive a selection of a feature of a presentation panel by a user; and highlighting circuitry 28 configured to highlight a feature of a further presentation panel.

In the present embodiment, the circuitries 24, 26, 28 are each implemented in computing apparatus 12 by means of a computer program having computer-readable instructions that are executable to perform the method of the embodiment. However, in other embodiments, the various circultries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
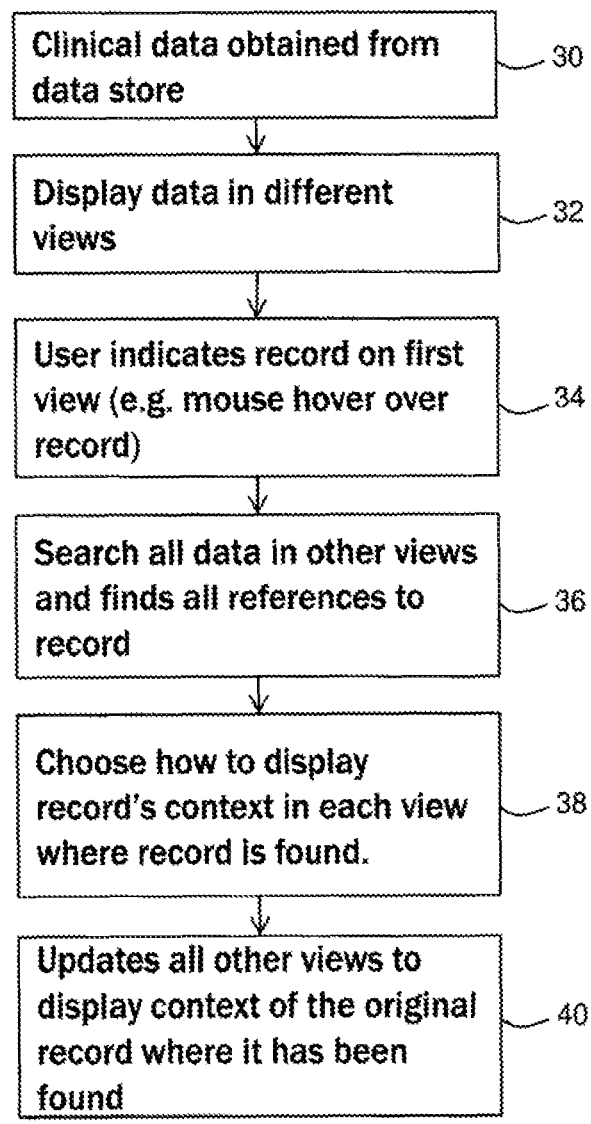
FIG. 2 is a flow chart illustrating in overview a process performed in accordance with an embodiment.
Figure 3:
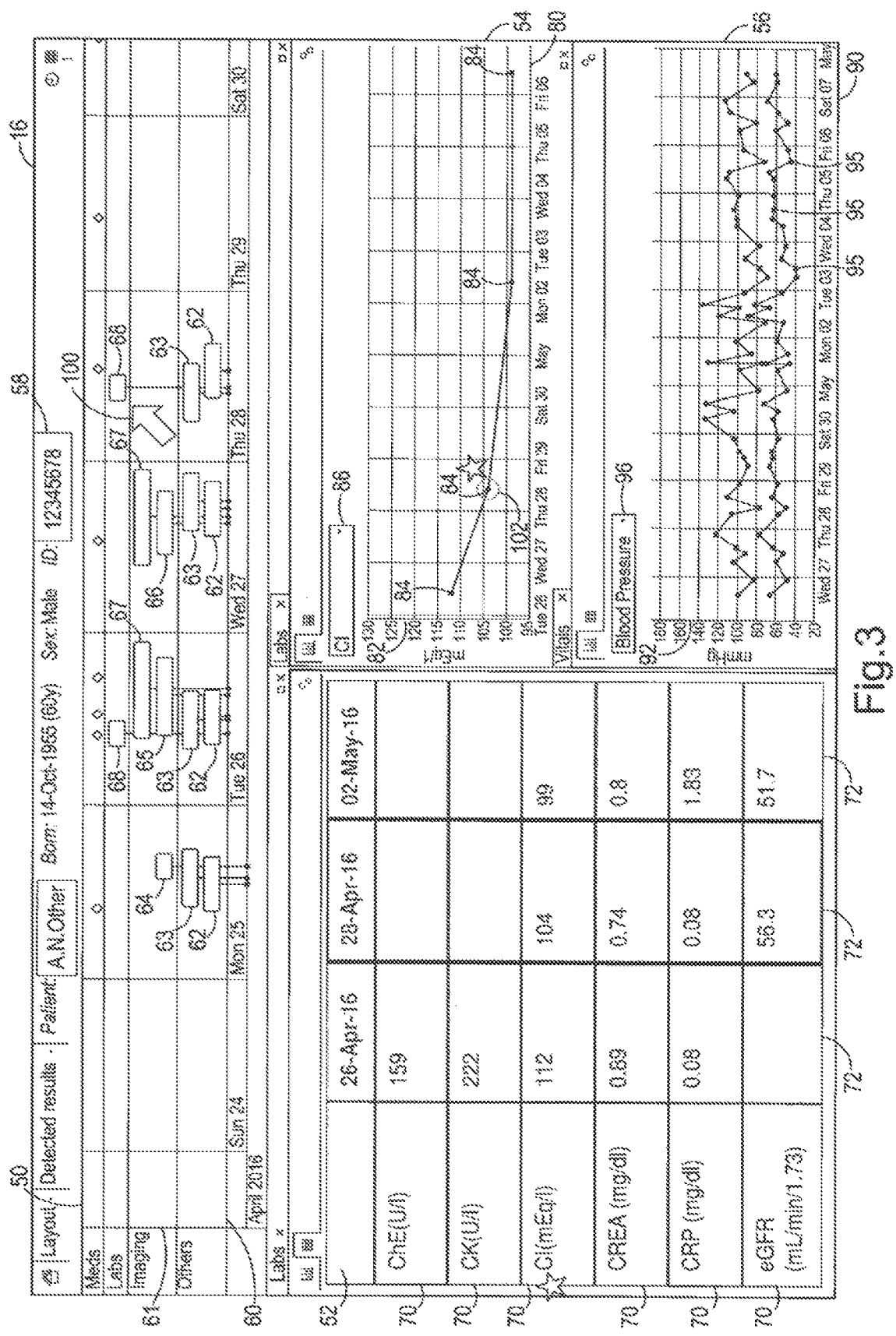
FIG. 3 is a schematic illustration of a multi-panel display in accordance with an embodiment, showing highlighting on hover.

The system of FIG. 1 is configured to perform a series of stages as illustrated in overview in the flow chart of FIG. 2 with reference to the schematic illustration of FIG. 3.

At stage 30, the display circuitry 24 obtains medical data from data store 20. The medical data relates to a patient.

The medical data comprises a plurality of medical records. We note that the term medical record in this context may be used to refer to any set of recorded information that relates to the patient. The term medical record may in some circumstances also may be used to refer to the totality of data held for a patient. However, in the description below we use medical record to refer to an individual set of recorded information.

Each medical record may comprise, for example, a clinical note, a nursing note, a set of imaging data, a set of imaging measurements, a set of lab result data, a set of patient monitoring data, a set of vital sign data, a prescription, a medication record, data obtained from the patient, data obtained from a medical device, a summary report, a medical history report, a case conference report, a billing report, a radiology report, a set of patient events, medication data, administration or records data or any other suitable set of recorded information relating to the patient or other subject.

In the present embodiment, the medical data obtained by the display circuitry 24 includes all the medical records available for that patient. In other embodiments, the medical data obtained by the display circuitry 24 may comprise a subset of the medical records available for that patient, for example medical data pertaining to treatment in a certain hospital, by a certain doctor, in a certain department or relating to a certain specialty (e.g. oncology department) or within a certain time range.

Although in the present embodiment the medical data is obtained only from data store 20, in other embodiments the medical data may be obtained from any suitable data store or data stores, for example from multiple servers on a network.

The medical data may be formatted in any suitable electronic format, for example any known format for electronic medical record data. DICOM structured reports are one such possible format. In some embodiments, different medical records may have different data formats. For example, different medical records may be obtained from different data stores that use different data formats, or different types of medical data may be recorded in different formats. Some data may be structured and some may be unstructured (for example typed notes made through computer input or scanned copies of clinical notes).

At stage 32 of the flow chart of FIG. 2, the display circuitry 24 displays some of the medical data on a plurality of presentation panels 50, 52, 54, 56, 58. The presentation panels may alternatively be referred to as views or windows. Different presentation panels display data using different presentation formats. The same data or corresponding data may be displayed differently in the different presentation formats. For example, a set of lab results may be represented as a box on a time line view and as a table of results in a table of results view. Details of the different presentation formats are described below.

In the present embodiment, each of the presentation panels is configured such that it may be individually manipulated by a user. For example, the user may reposition, close, or resize each of the presentation panels, or pen, zoom or scroll data or other content in the panels. In other embodiments, some of the parameters of one or more of the presentation panels may be fixed such that they may not be manipulated by a user.

In FIG. 3, the first presentation panel 50 comprises a time line view. A horizontal axis 60 of the time line view represents time. In the embodiment of FIG. 3, time is shown in days and a total range of about a week is shown. In other embodiments, time may be shown on any suitable scale and in any suitable increments, for example hours, minutes, weeks or months. A user may adjust the time scale shown by using any suitable commands, for example by panning or zooming.

Medical records are presented by boxes which are positioned relative to the horizontal axis 60 in accordance with a time associated with each of the medical records. The boxes are also grouped by the type of medical record that they represent.

In the embodiment of FIG. 3, the boxes are grouped vertically relative to a vertical axis 61 in dependence on whether they represent medication (Meds), laboratory results (Labs), imaging results (Imaging) or other records (Others).

In the embodiment shown in FIG. 3, the boxes representing the medical records comprise boxes representing clinical notes 62; nursing notes 63; sets of imaging data (electrocardiogram data 64, chest X-ray imaging data 65 and echocardiogram data 66); sets of imaging measurement data 67; and sets of lab result data 68. In the description below, references to the medical records 62, 63, . . . 68 in the first presentation panel 50 may refer both to the medical records themselves and to the boxes representative of those medical records in the first presentation panel 50. The diamonds shown in the figure in this embodiment indicate a giving of medication to the patient or a change in any kind of medicine administration.

Each clinical note 62 comprises text information regarding an encounter between the patient and a clinician or regarding any other suitable event or analysis, for example text information relating to test results received from a laboratory or other testing facility. The text information is not shown in presentation panel 50, which shows each clinical note 62 as a respective box. Each nursing note 63 comprises text information regarding an encounter between the patient and a nurse. In other embodiments, the term clinical note or medical note may encompass nursing notes or notes recorded by any medical professional.

Each clinical note 62 or nursing note 83 has at least one associated time, for example the time at which the encounter recorded in the note took place and/or the time at which the note was recorded. The clinical notes 62 and nursing notes 63 are positioned relative to the time line axis 60 in accordance with their associated times.

The set of electrocardiogram (ECG) data 64 comprises data obtained from an ECG at an associated time, which may be a time at which data acquisition started. The set of chest X-ray imaging data 65 comprises data obtained from a chest X-ray at an associated time. The set of echocardiogram imaging data 66 comprises data obtained from an echocardiogram at an associated time. Each of the ECG data 64, chest X-ray imaging data 65, and echocardiogram imaging data 6 is positioned relative to the time line axis 60 in accordance with its associated time. This data is primarily relevant for a cardiology patient. Different types of data may be presented for different clinical cases, for example stroke patients.

The data that is included in the display panels of FIGS. 3 to 7 and 9, for example the notes data, is included purely by way of example, and any other suitable data may be included.

For example, notes could be provided under various headings or in various categories for instance Subjective (for example, whether the patient is in acute distress), Physical Examination, Laboratory Data, Diagnostic Studies, Assessment and Plan.

Physical Examination notes could for example includes notes for Vital Signs (e.g. blood pressure, pulse and oxygen saturation values), Head and Neck (e.g. whether face is symmetrical, whether cranial nerves are intact), Chest (expiration or inhalation properties, such as presence of prolonged expiration), Cardiovascular (e.g, whether first and second heart sounds are heard, whether murmur present), Abdomen (e.g, whether soft/hand and tender/nontender, nature of bowel sounds), Extremities (e.g, presence of pedal swelling), Neurologic (e.g, whether patient is asleep/awake and whether arousable), Laboratory Data notes in a cardiac example could include, for instance values for PTT, INR, BUN, AST, ALT and creatinine, sodium and potassium values.

Diagnostic Studies notes in a cardiac example could include, for example, nuclear stress test results and election fraction values.

Assessment and Plan notes could include, for example, notes on the likely presence or absence of various conditions or symptoms, and current, proposed or potential treatments or actions in relation to such conditions or symptoms. In a cardiac example such conditions or symptoms could include for example congestive heart failure, rapid atrial fibrillation, systolic dysfunction, acute pulmonary edema, rapid atrial fibrillation, coronary artery disease, ischemic cardiomyopathy, urinary tract infection, bilateral perfusion, chronic obstructive pulmonary disease, abnormal liver function, hypercholesterolemia, tobacco smoking disorder, hyponatremia, deep venous thrombosis.

Imaging measurements 67 comprise measurement data that is obtained from imaging data, for example by a radiologist or radiographer or automatically. In FIG. 3, imaging measurements are obtained from chest X-ray imaging data 65 and echocardiogram imaging data 66. Each set of imaging measurements 67 are obtained on the same data as their associated imaging data 66, 66 and are positioned on the time line axis 60 accordingly.

Lab result data 68 may comprise the results of any suitable set of lab tests, for example blood tests or urine tests. Each set of lab result data 68 has associated time, for example a time which the lab results were acquired and/or recorded. The sets of lab result data 68 are positioned relative to the time line axis 60 in accordance with their associated times.

In other embodiments, any type of indicator (for example, boxes, dots or any suitable shape of indicator) may be used to represent any type of medical records and/or time ranges on the first presentation panel. For example, an indicator could be used to represent a time or time period for administration of a selected medication.

Any suitable presentation of the time line axis may be used. For example, the time line may be horizontal or vertical. In some embodiments, all medical records in the time period shown on the time line axis are displayed. In other embodiments, only selected medical records or selected types of medical records may be shown. The presentation panel may be configured such that a user may select particular medical records or categories of medical records for display. For example, referring to FIG. 3, a user may choose to display only Meds and Labs while hiding imaging and Others.

The second presentation panel 52 comprises a table of results. The table of results comprises a plurality of rows 70, each representing a different lab test, and a plurality of columns 72, each representing a time (for example, a date) at which lab results were obtained. The second presentation panel 52 therefore comprises a different type of presentation (table of results) from the presentation of the first presentation panel 50 (time line view). A set of lab results 68 that is represented as a box in the first presentation panel 50 may be represented by a table of results in the second presentation panel 52.

In other embodiments, the table of results may represent any appropriate numerical data. The table of results may represent lab results, for example results of blood tests or urine tests. The table of results may represent data relating to a patient's vital signs, for example blood pressure. The table of results may represent measurements, for example imaging measurements. Alternatively or additionally, the or a table that may be included in the display may comprise a list of medications, which may for example include dosage and times or periods of times when the dosages of the medication should be given.

In FIG. 3, a subset of the available lab result data is displayed at any one time. Further lab results may be obtained by scrolling the second presentation panel 52 vertically. Lab results for further dates may be obtained by scrolling columns 72 of the second presentation panel 52 horizontally.

The third presentation panel 54 is a plot, which in the present embodiment is a plot of blood chloride measurements. The horizontal axis 80 of the third presentation panel 54 shows time, and the vertical axis 82 shows blood chloride in milliequivalents of chloride per liter of blood (mEq/L). Each measurement of blood chloride is represented by a respective point 84 on the plot. The third presentation panel is configured such that the user may change the lab result displayed from blood chloride to a different lab result by using a drop-down menu 86 to select from a list of lab results. In other embodiments, the user may select which result to show and/or a time scale and/or range for the plot using any suitable selection method. For example, the user may type in a lab result to show. The user may scroll the third presentation panel horizontally to show results for different dates.

The third presentation panel 54 therefore provides a further type of data presentation (which may be referred to as a plot or graph) which is different from the data presentations of the first presentation panel 50 (time line) and second presentation panel 52 (table of results). A single set of lab results 68 may be represented differently in the different types of data presentation.

The fourth presentation panel 56 is a plot, which in the present embodiment is a plot of blood pressure measurements. The horizontal axis 90 of the fourth presentation panel 58 shows time, and the vertical axis 92 shows blood pressure in millimeters of mercury (mmHg). Blood pressure measurements are represented by points 94, 95 on the plot. The fourth presentation panel is configured such that the user may change the vital sign displayed from blood pressure to a different vital sign by using a drop-down menu 96 to select from a list of vital signs. In other embodiments, the user may select which vital sign to show and/or a time scale and/or range for the plot using any suitable selection method.

The fifth presentation panel 58 shows identifying data for the patient, which in this embodiment comprises the patient's name, date of birth and ID number. In other embodiments, any appropriate identifying information may be shown.

In other embodiments, any combination of presentation panels may be displayed. The presentation panels shown may include two or more different types of presentation panel. For example, the presentation panels shown may comprise two or more of a time line, a table of results, a list of results, a chart, a plot, a graph, a trend graph over time, a text narrative, a display of patient identifying data, a display of imaging data, a collection of patient timeline events (e.g. date of admission to hospital, date of surgery etc), a report document (e.g. a pdf file). One or more panels may include overlay or annotations, for example overlays, annotations or measurements on imaging data. The overlay or annotations may for example comprise additional data created based on analysis of raw or other data, such as scan data. Each presentation panel may comprise any suitable data presentation for displaying data relating to the patient.

The presentation panels may be arranged in any suitable arrangement on display screen 16, or on any appropriate display screen or screens. In some embodiments, the presentation panels are arranged in a default arrangement initially. In some embodiments, a user may be able to modify the default arrangement, for example by opening or closing panels or by repositioning or resizing panels.

The default arrangement may be selected to provide a standardized presentation of data to the user. The default arrangement may be selected such that the user always sees patient data in a standardized view, at least initially, so that the user becomes familiar with navigating the standardized presentation of data.

Turning again to the flow chart of FIG. 2, at stage 34 a user indicates a medical record on a first view, which in this embodiment is the first presentation panel 50. The user selects the medical record on the first presentation panel 50 by hovering over that medical record using a cursor 100. In the present embodiment, the cursor 100 is represented by an arrow. In other embodiments, any type of cursor may be used.

In further embodiments, any suitable method may be used to select the medical record. For example, the medical record may be selected by touching a touch screen or performing any suitable gesture on that touch screen. The medical record may be selected by tabbing between records. The medical record may be selected by performing any suitable action, for example an action comprising at least one of: a hover action, a click, a dragging action, a touch action, a swipe, a gesture, a voice input, a keyboard input, a mouse input, eye tracking or entering a record identifier.

In the embodiment of FIG. 3, the medical record that is selected is a set of lab results 68 having an associated data of Thursday 28 Apr. 2016. The selection circuitry 26 receives the user's selection of the set of lab results 68.

At stage 36, in response to the selection of the set of lab results 68, the highlighting circuitry 28 searches the other views to find all references to the set of lab results 68. In other embodiments, the highlighting circuitry 28 may search for only some references to the lab results 68. In some embodiments, the searching may include searching across one or more panels that are not currently open, or searching of content that could be included in panels, even if not currently displayed.

In the present embodiment, the other views are presentation panels 52, 54, 56, 58. The highlighting circuitry 28 determines whether any of presentation panels 52, 54, 56, 58 contain information that is part of or related to the set of lab results 68. In other embodiments, the highlighting circuitry 28 may be configured to search any one or more of the presentation panels 52, 54, 56, 58. In some embodiments, the user may select which of the presentation panels to search.

The highlighting circuitry 28 determines that presentation panels 52 and 54 contain information relating to the set of lab results 68. The table of results of presentation panel 52 contains a column 72 that is representative of at least some of the set of lab results obtained on 28 Apr. 2016. The plot of presentation panel 52 comprises a data point 84 that is representative of data (in FIG. 3, a blood chloride level) that is part of the set of lab results 68.

At stage 38 of FIG. 2, the highlighting circuitry 28 determines how to display the context of data from the set of lab results 68 in each view in which data from the record is found. Any suitable display method or methods may be used. For example, data may be highlighted by changing a text color, changing a background color, changing a text format (for example, bolding, italicizing or changing typeface), using an indicator (for example, a pointer, box or balloon), using an animation, animating an existing feature, or overlaying an indicator or other feature. Any suitable animated effect may be used for highlighting, for example flashing, pulsing, a change in color over time, a change in style over time, a moving indicator.

In the present embodiment, the highlighting circuitry 28 selects only display methods that do not involve moving any of the displays of the presentation panels (for example scrolling or zooming the presentation panels). The highlighting is applied without otherwise changing the data presentation and/or position.

In the present embodiment, the highlighting circuitry 28 determines three methods of displaying context. The highlighting circuitry 28 determines that the data point 84 that relates to the selected lab results 68 should be highlighted by a flashing pulse at the data point 84. The highlighting circuitry 28 determines that the column of results 72 relating to the selected lab results 68 should be highlighted by a box outlining the appropriate column of results 72. The highlighting circuitry 28 may also determine that the connection between the blood chloride value in the table of results of presentation panel 62 and the representation of blood chloride value in the plot of presentation panel 54 should be highlighted and may present an indicator to provide such highlighting.

At stage 40, the highlighting circuitry updates presentation panel 52 and presentation panel 54 to display the context of the information relating to the selected set of lab results 68.

The highlighting circuitry 28 highlights the date point 84 that is pert of the selected set of lab results 68 by using a flashing pulse, which is represented on FIG. 3 by circle 102. The highlighting circuitry 28 highlights the column of results 72 that includes results that are pert of the set of lab results 68 by providing a solid box 104 outlining the column of results 72. The highlighting circuitry 28 may, it desired, provide an indicator that indicates the blood chloride result from the set of lab results 68 on the plot of presentation panel 54 and the corresponding entry in the table of results of presentation panel 52.

In some embodiments, the highlighting circuitry 28 also highlights the selected medical record, for example by changing the color of the box representing the selected medical record in the first presentation panel 50.

In some embodiments, the highlighting circuitry 28 highlights the presentation panels that contain information relating to the selected medical record, for example by changing the color of each panel that contains such information, or by outlining each panel that contains such information.

In other embodiments, any appropriate method of highlighting may be used to highlight any appropriate data relating to the selected medical record.

In further embodiments, any feature of any of the presentation panels may be selected at stage 34, which may not be a representation of a medical record as in the current embodiment. For example, the selection circuitry 26 may receive a selection by a user of any of at least one numerical value, a numerical range, at least part of a text entry, a time, at least part of a table of results, at least part of a clinical note, at least part of a medical record.

Any feature of any of the presentation panels may be highlighted by the highlighting circuitry 28, for example at least one data item of the medical data, at least one numerical value, at least one numerical range, a scale or part of a scale, at least part of a text entry, a time, at least part of a table of results, at least part of a clinical note, at least part of a medical record.

The feature or features that are highlighted by the highlighting circuitry 28 may each comprise data that is part of, or otherwise relates to, the feature for which a selection is received by the selection circuitry 26. Each feature that is selected or highlighted may be any part of a presentation panel that is representative of part or all of a medical record.

The embodiment described above with reference to FIGS. 1 to 3 provides a graphical user interface for automatically highlighting matching clinical data records across different presentation areas. An application is made up of presentation views (e.g. panels) that present clinical information that may include a display of uniquely identified clinical data records in differing formats and within different context.

The user may select a record of interest (for example, by hovering on the record or double clicking). The system may automatically highlight any appearance of data from, or corresponding to, the same clinical data record as it appears in different presentation views. The highlighting may be, for example, by animation, or by a change of style of text.

By providing highlighting of data in different views, the medical data presented in the presentation panels may become more easily usable by the user.

As the amount of data captured for a given patient by hospital systems increases, it may become difficult for a user (for example, a clinician) to navigate the data available. The user may have to open may different electronic documents and read or otherwise scan through each document to obtain the required information.

A multi-panel clinical review display, which may for example be referred to as a dashboard, may assist the user in viewing several different types of presentation at once. By providing highlighting of features relating to an initial selected feature, the user may be informed of the context of the selected feature. For example, in the case shown in FIG. 3, from a starting point of selecting the set of lab results 68 in the time line of presentation panel 50, where the user can see where the set of lab results 68 occurred in time, the user is also shown how the lab results 68 fit into the context of other lab results in the table of results of presentation panel 52, and how each an individual lab result from the set of lab results 68 fits into a time variation of that lab result in presentation panel 54.

Using the method described above with reference to FIGS. 1 to 3 may reduce the chance of the clinician missing important contextual information. A speed of accessing information may be increased. The clinician may be able to gain information more quickly and/or make faster clinical decisions. The clinician may be able more easily to connect representations of the same or corresponding data in different presentation panels due to the highlighting. The clinician may not have to re-find a record of interest when looking at a new context, for example a new presentation panel.

The method described above with reference to FIGS. 1 to 3 may be used to display data from a variety of sources. The data may have different data sources. By displaying the data having different sources and/or formats in a consistent presentation, it may be more easily comprehended by the user, for example by a clinician. The apparatus may connect data from different sources and/or in different formats by highlighting, which may allow the user to easily connect disparate data.

In the embodiment of FIG. 3, data is highlighted in the presentation panels without otherwise changing the presentation panels. The presentation of data may therefore be augmented by the provision of the highlighting, without making any changes that may make the presentation more confusing to the user. The user may see a display that they originally expected or chose to see, with only the addition of highlighting to highlight certain features. The highlighting functionality may be provided on any display that is chosen by the user.

The method described above with reference to FIGS. 1 to 3 may be used in clinical contexts in which a very large amount of information is available and/or in clinical contexts in which data must be analyzed in a very short period of time.

In some embodiments, the method of FIGS. 1 to 3 may, for example, be used to view data for a patient who is suspected to have had a heart attack, other cardiac incident or a stroke. The time line of presentation panel 50 may be configured to display a short time, for example a few hours. In that short time, a large amount of data (for example, imaging, lab tests and clinical notes) may be acquired for the patient.

In hyper acute environments (for example, stroke) certain therapy options may be time bound. For example, the use of a clot busting thrombolytic drug such as alteplase may be indicated within 3.5 hours of stroke symptoms onset. It may therefore be important to determine if this therapy option is suitable as soon as possible, otherwise the patient may be excluded from a potentially highly effective treatment.

By receiving a user selection of a feature and highlighting corresponding features in other presentation panels, the clinician may navigate the data more quickly. Speed may be particularly important in the treatment of stroke. Providing treatment within the golden hour (the first hour after the onset of stroke symptoms) may be critical.

In another embodiment, the method is used in cardiology. In a further embodiment, the method of FIGS. 1 to 3 is used in oncology. The time line of presentation panel 50 may be set to a longer time, for example weeks or months.

In oncology, patients may normally be staged during their initial diagnostic investigation. The staging may include a combination of imaging, lab test, biopsies and possibly genetic tests. Staging information may be used to help in therapy planning. Staging information may be used at subsequent follow up reviews. Follow up reviews may happen weeks or months after treatment. Follow up reviews may be used to check if a particular therapy pathway has been effective at tackling a specific cancer. Having a flexible timeline presentation may allow different time periods to easily be compared and reviewed.

Some examples of selection and highlighting are described above with reference to FIG. 3. Embodiments describing further combinations of selection and highlighting are described below with reference to FIGS. 4 to 8 and 9.

Figure 4:
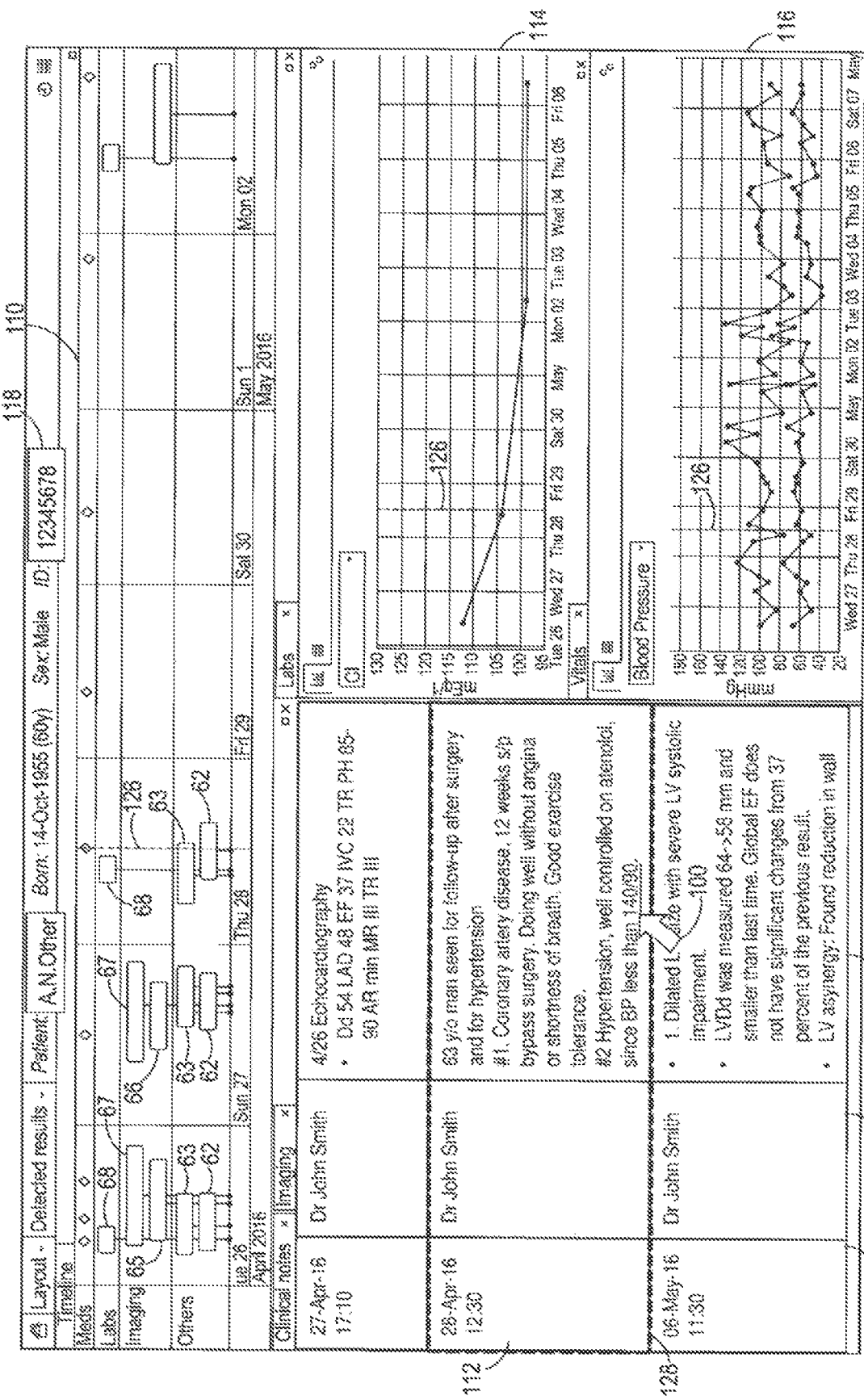
FIG. 4 is a schematic illustration of a multi-panel display in accordance with an embodiment, showing highlighting of a record timestamp in other panels.

FIG. 4 shows a display of medical data in a plurality of different views, which in the embodiment of FIG. 4 comprise a plurality of presentation panels 110, 112, 114, 116, 118.

Presentation panel 110 is a time line view showing a plurality of medical records 62, 63, 65, 66, 67, 68.

Presentation panel 112 is a table of clinical notes. A simplified version of the table of clinical notes is shown in FIG. 4. In practice the clinical notes may be considerable longer and more detailed. Column 120 shows the date and time of each clinical note. Column 122 shows the clinician who recorded the clinical note. Column 124 shows the narrative text of the clinical note.

Presentation panel 114 is a plot of blood chloride results. Presentation panel 118 is a plot of blood pressure results. Presentation panel 118 shows patient identifying information. Presentation panels 110, 114, 116, 118 are similar to presentation panels 50, 54, 56, 58 of FIG. 3.

In the embodiment of FIG. 4, a user indicates a reference to a vital sign measurement of presentation panel 112 by using a cursor 100 to hover over the reference to the vital sign measurement in one of the clinical notes shown on presentation panel 112.

The selection circuitry 24 receives the selection of the vital sign measurement. The vital signal measurement has a corresponding time of record, which may be referred to as a timestamp. The highlighting circuitry highlights the time of record on other panels that show a time based display, which in the embodiment of FIG. 4 are the time line view of presentation panel 110, and the plots of presentation panels 114 and 116. The time of record is highlighted on the other time based panels for comparison of different clinical data at the same point in time.

The time of record is shown in each of presentation panels 110, 114 and 116 using a dotted line 126. In other embodiments, any suitable indicator may be used to indicate the time of record.

In the present embodiment, the highlighting circuitry 28 also highlights the clinical note in which the vital sign measurement is present by using a dotted box 128 and highlights the vital sign measurement itself by underlining.

In other embodiments, the highlighting circuitry 28 may also highlight a point on the plot of presentation panel 116 that is representative of the vital sign measurement. The highlighting circuitry 28 may highlight the clinical note 62 comprising the vital sign measurement on the time line of presentation panel 110.

In further embodiments, any selection of any appropriate feature in any one of the presentation panels may cause an associated time or time range to be highlighted in any other of the presentation panels. For example, selection of a medical record in the presentation panel 110 may cause a time associated with that medical record to be highlighted in the plot of presentation panels 114 and/or 116. Selection of a point in the plot of presentation panel 114 and/or 116 may cause a time associated with that point to be highlighted in the time line of presentation panel 110. A clinical note corresponding to a selected time may be highlighted in presentation panel 112.

In some embodiments, only features having exactly the same time as a selected item are highlighted. In other embodiments, features having close or related times may be highlighted. For example, on selection of a medical record in presentation panel 110, the highlighting circuitry 28 may highlight the one of the clinical notes shown in presentation panel 112 that is closest in time to a time of the selected medical record.

In some circumstances, medical records that are related to each other may be recorded close in time rather than at exactly the same time. For example, imaging data may be acquired at a first time, measurements may be obtained from the imaging data at a second time, notes may be written regarding the medical data at a third time, and imaging results may be reported to a patient at a fourth time. In some circumstances, highlighting of a feature having one associated time (for example, clinical notes associated with a time of recording of those notes) may cause a different time to be highlighted in other presentation panels (for example, the time of a set of imaging data to which the clinical notes relate).

In some embodiments, the feature that is selected is a time on one of the time-based panels (for example, presentation panel 110) that is not a time associated with a medical record. The selected time may be highlighted on other time-based panels.

In some embodiments, the user selects a time range in one of the time based panels, for example by clicking and dragging a mouse. The selected time range is highlighted on other time-based panels. In some embodiments, the highlighting circuitry 28 is configured to change the scale of one or more of the time based panels in dependence on the selection of a time range on a different one of the time based panels. In one embodiment, the selection circuitry 26 receives a selection of a time range in presentation panel 110 and alters a scale of the plots of presentation panels 114 and 116 such that they only show the selected time range.

By showing corresponding times in the different panels, the user may find it easier to navigate the data in the different panels. The user may understand the context of a particular medical record or part of a medical record by being shown what is happening at the same time.

Figure 5:
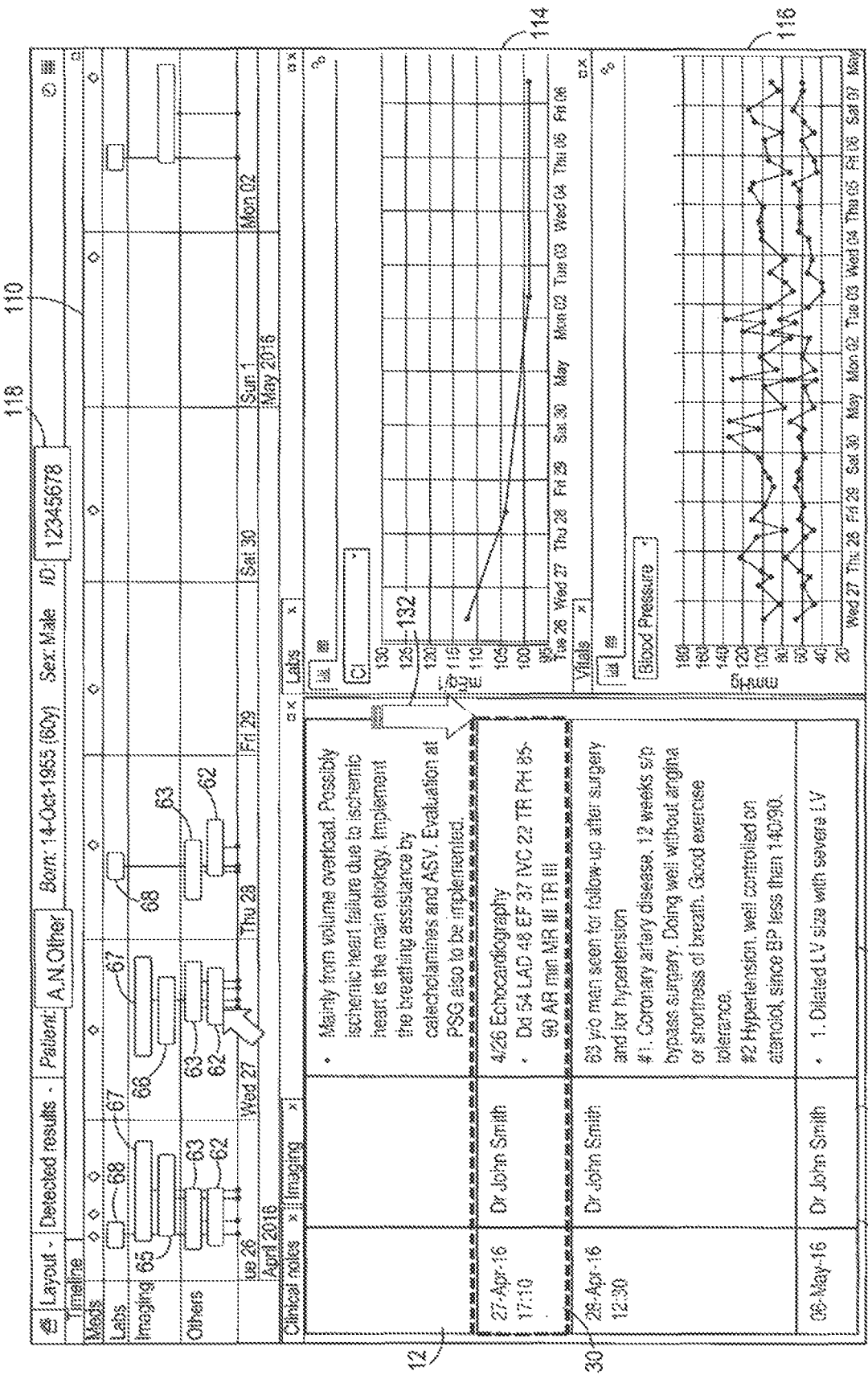
FIG. 5 is a schematic illustration of a multi-panel display in accordance with an embodiment, showing automatic scroll for visibility of matching data.

FIG. 5 shows the same presentation panels 110, 112, 114, 116, 118 as FIG. 4. In the embodiment of FIG. 5, the selection circuitry 26 receives a selection of a clinical note 62 on the time line of presentation panel 110.

In response to the selection, the highlighting circuitry 28 identifies the corresponding clinical note on the clinical note display of presentation panel 112. The same clinical note is shown in presentation panels 110 and 112 using different data presentations.

In the embodiment of FIG. 4, it happens to be the case that the corresponding clinical note is not visible on the clinical note display of presentation panel 112, which shows only a portion of the clinical notes available.

Therefore, the highlighting circuitry 28 scrolls the clinical note display of presentation panel 112 such that the relevant clinical note is visible, in addition to highlighting the relevant clinical note with a dotted box 130. The scrolling action is represented by arrow 132 (which is not shown on the display in practice).

In other embodiments, any suitable action may be performed on any one of the presentation panels to display data corresponding to a selected feature. For example, a display may be scrolled, panned, or zoomed instead of or in addition to being highlighted using, for example, color, outlining or text style. The display may be scrolled or penned such that the relevant data is centered on the panel. Alternatively, the display may be scrolled, panned or zoomed using a minimum possible action to make the relevant data visible. For example, the clinical notes display of presentation panel 112 may be scrolled down until the required clinical note becomes just visible at the top of presentation panel 112 (or scrolled up until the required clinical note becomes just visible at the bottom of presentation panel 112).

In the embodiment of FIG. 5, upon hovering on a clinical note on a time line, the panel 112 automatically scrolls to make the clinical note visible in the panel 112 and also highlights it with a border 130, which may be an animated border.

In other embodiments, any presentation panel may automatically scroll to show relevant data. For example, the plots of presentation panels 114 and 116 may be scrolled horizontally to show appropriate data points. The time line of presentation panel 112 may be scrolled horizontally to show a medical record related to a feature that has been selected on one of the other presentation panels.

Figure 6:
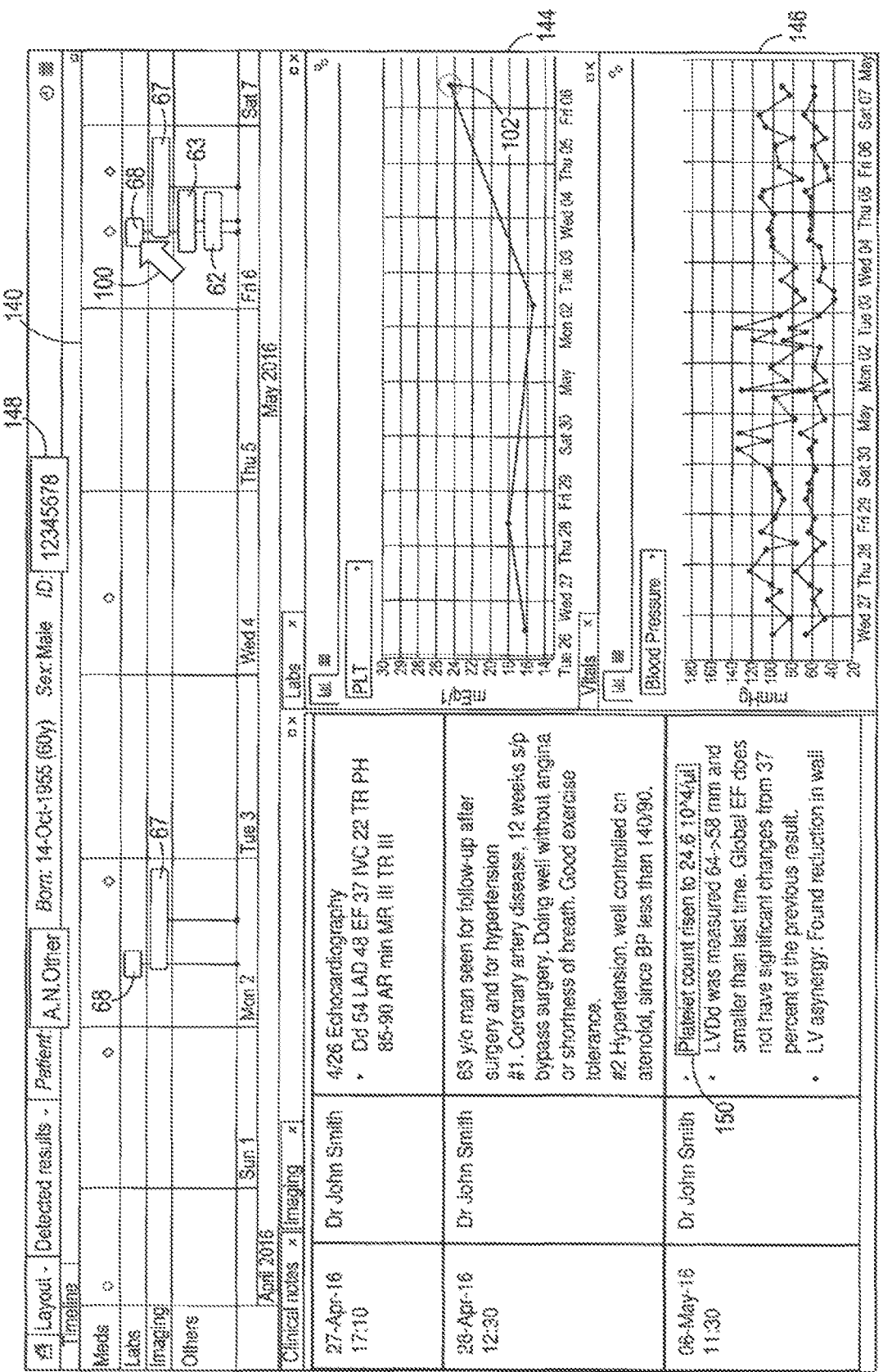
FIG. 6 is a schematic illustration of a multi-panel display in accordance with an embodiment, showing textual highlight of record reference.

FIG. 6 shows a plurality of presentation panels 140, 142, 144, 146, 148, which are similar to the presentation panels 110, 112, 114, 116 and 118 but represent a different range of time. Presentation panel 144 shows a different lab result (platelet count) from that shown in presentation panel 114.

In the embodiment of FIG. 6, upon hovering on a lab record 68 using cursor 100 in the time line of presentation panel 140, a clinical note referring to the same record is highlighted. In response to the selection, the highlighting circuitry 28 searches for references to the lab record 68 and finds a text reference in the clinical notes of presentation panel 142 and a data point in the plot of presentation panel 144.

The highlighting circuitry 28 highlights the text reference by changing the background color of a region 150 surrounding the text reference. In the present embodiment, the text reference within the clinical note is highlighted. In other embodiments, the entire clinical note may be highlighted. However, by highlighting the text reference instead of or in addition to the entire clinical note, the clinician may find it easier to navigate the data provided (especially since in practice the clinical notes may be much longer than the clinical notes shown in FIG. 6). In some embodiments, natural language processing may be used to generate text for output based on the clinical note or a part of the clinical note.

The highlighting circuitry 28 also highlights the data point in presentation panel 144 by using a flashing pulse, which is represented on FIG. 6 by circle 102.

Figure 7:
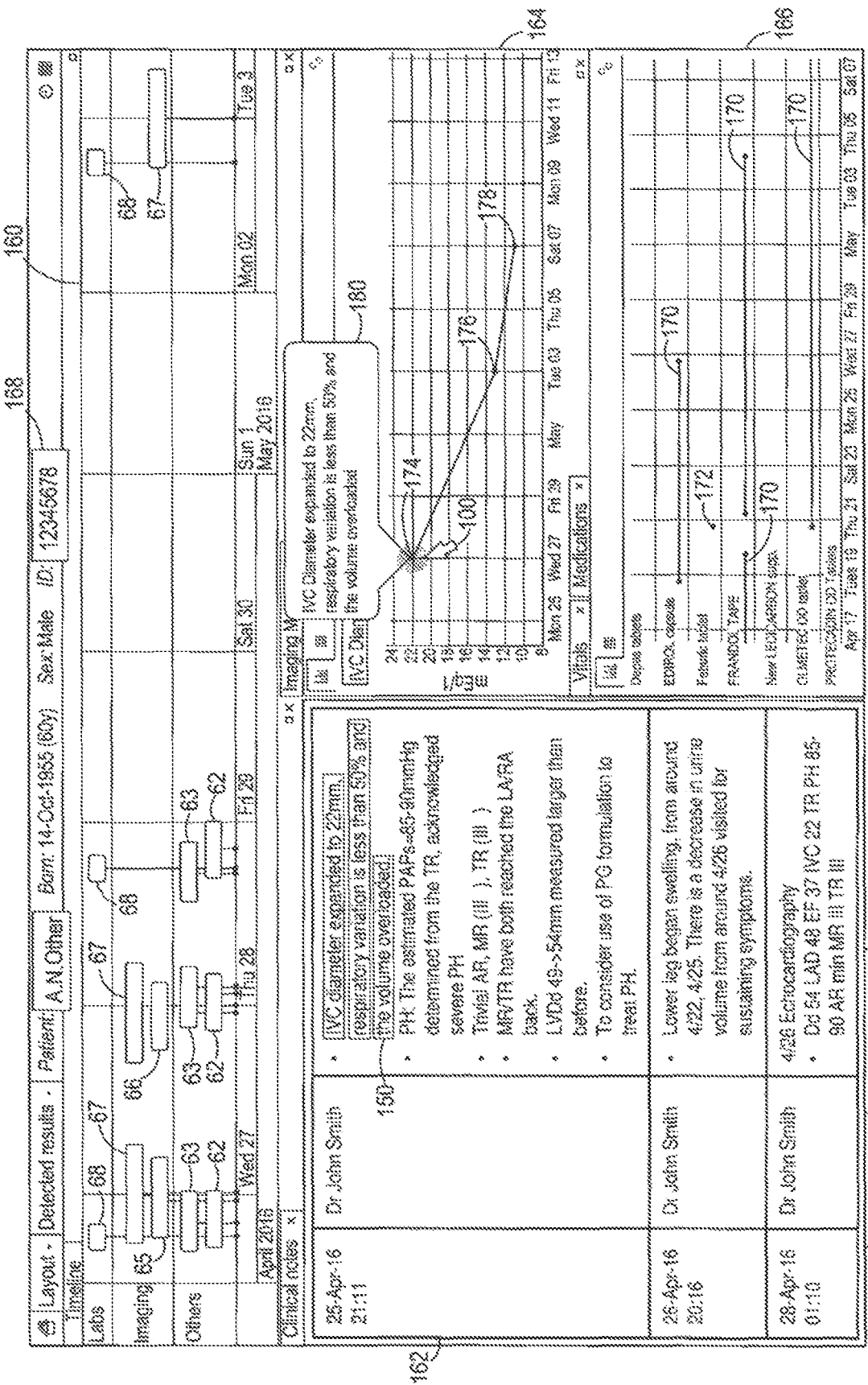
FIG. 7 is a schematic illustration of a multi-panel display in accordance with an embodiment, showing the highlighting of data described in clinical notes in a graph view.

FIG. 7 shows a plurality of presentation panels 160, 162, 164, 166, 168. Presentation panel 160 shows a time line view similar to that of presentation panel 110 of FIG. 4. Presentation panel 162 shows a clinical notes view similar to that of presentation panel 112 of FIG. 4.

Presentation panel 164 shows a plot of an imaging measurement, which in FIG. 7 is a plot of inferior vena cava (IVC) diameter. Presentation panel 164 shows three data points 174, 176, 178, each having an associated time.

Presentation panel 166 shows a plot of a plurality of medications. The length of time for which each of the medications is administered is shown as a bar 170 on presentation panel 166. A single administration of one of the medications is shown as a point 172. Presentation panel 168 shows patient identifying information and is similar to presentation panel 118 of FIG. 4.

In the embodiment of FIG. 7, the user hovers on a data point 174 in the graph view of presentation panel 164 using cursor 100. When the cursor 100 hovers on the data point 174, the highlighting circuitry 28 highlights text that includes data linked to data point 174 is highlighted by a changed background color of a region 150 including the text. Highlighting the linked text may allow the user to easily cross reference the plot of presentation panel 164 with a relevant part of the clinical notes of presentation panel 162.

Furthermore, when the cursor 100 hovers on the data point 174, the highlighting circuitry 28 provides a message 180 associated with (for example, adjacent to) data point 174. The message 180 appears in a balloon in response to the selection of the data point 174, which may be referred to as a tooltip. In other embodiments, any method of displaying the message 180 may be used. The message comprises text including the linked data from the clinical note.

Providing the message 180 as a tooltip may provide the user with a convenient format for viewing the linked text. Providing the message 180 as a tooltip may allow the user to see the relevant part of the clinical note without having to look at the rest of the clinical note, which may save time. In some embodiments, the relevant part of the clinical note may be displayed, for example using the tooltip or other mechanism, even if a panel for that clinical note is not open.

The highlighting circuitry 28 also highlights the selected data point 174 by displaying the data point 174 differently from the others, so that the user can identify which data is referred to the highlighted clinical note. In the embodiment of FIG. 7, the selected data point 174 is displayed as a larger data point than the other data points 176, 178 and with a halo.

Figure 8:
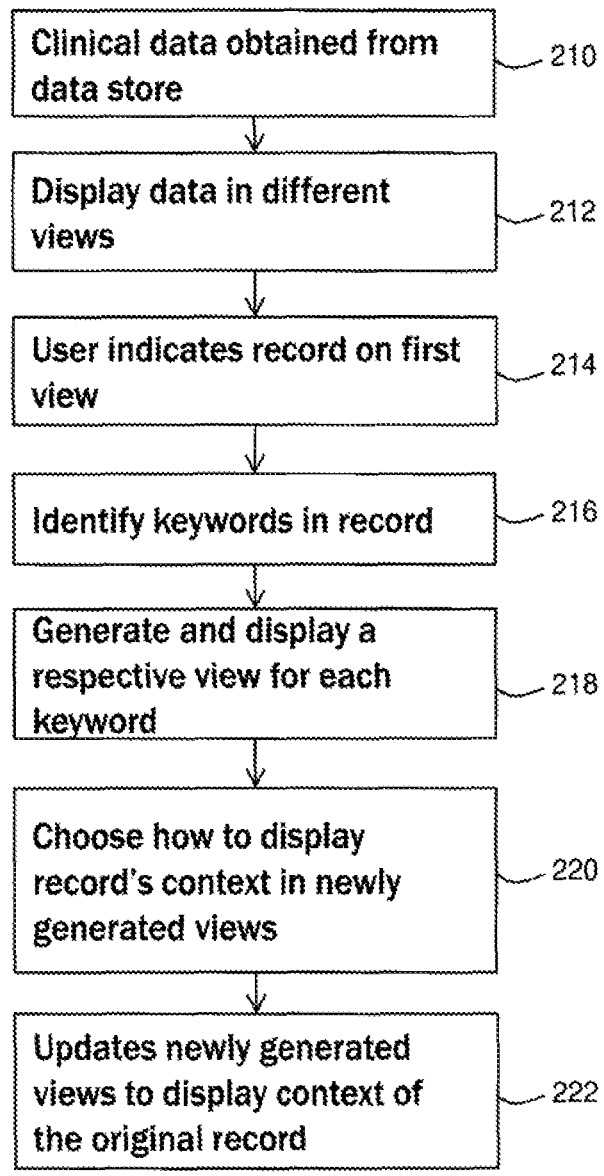
FIG. 8 is a flow chart illustrating in overview a process performed in accordance with an embodiment.

FIG. 8 is a flow chart illustrating a process of a further embodiment, which is described with reference to FIG. 9.

At stage 210 of the process of FIG. 8, the display circuitry 24 receives medical data from data store 20. The medical data comprises a plurality of medical records.

Figure 9:
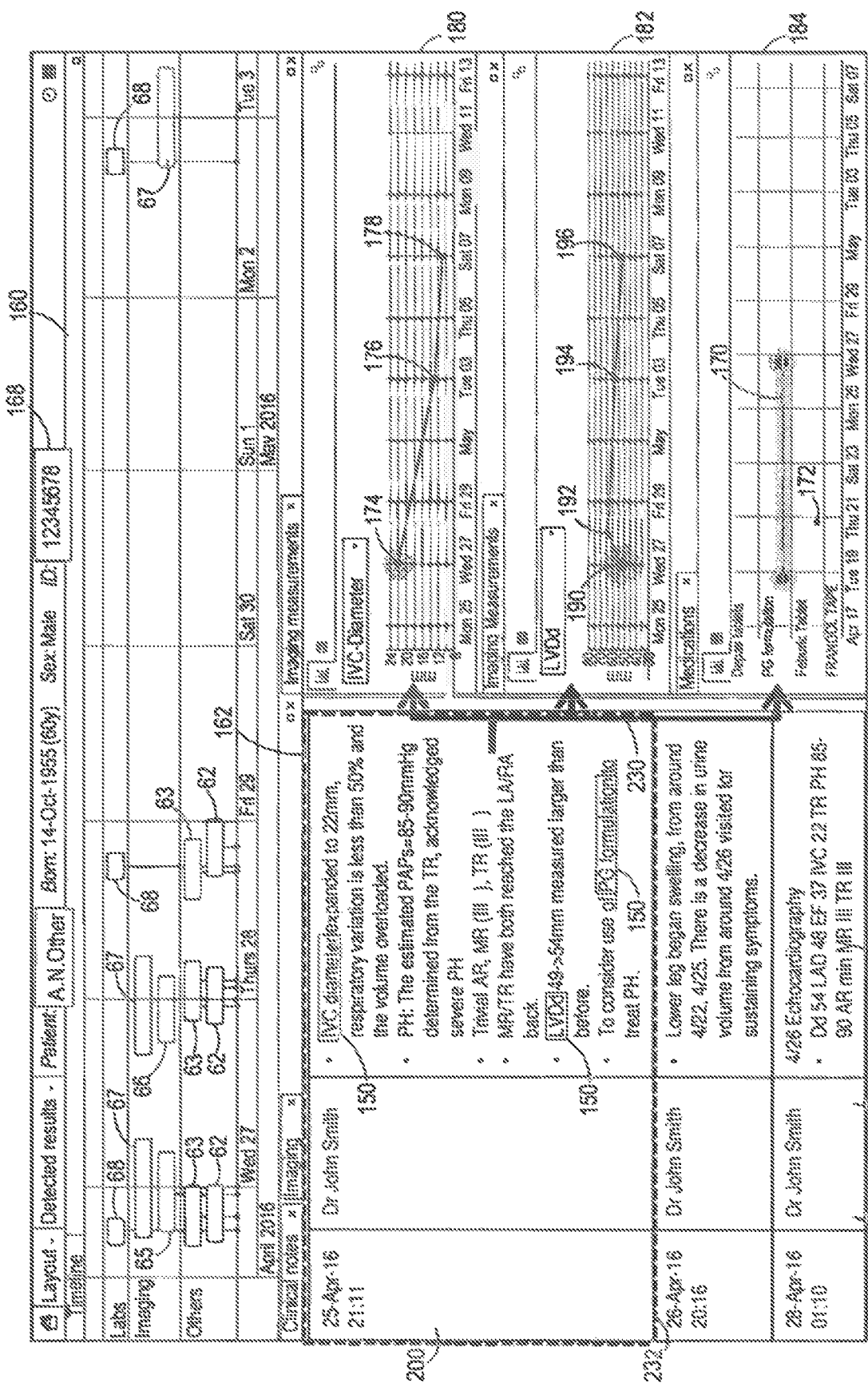
FIG. 9 is a schematic illustration of a multi-panel display in accordance with an embodiment, showing the highlighting of linked data in other views from clinical notes.

At stage 212, the display circuitry 24 displays some of the medical data in a plurality of presentation views, which include presentation panels 160, 162 and 168 of FIG. 9 and may include other panels not shown in FIG. 9. For example, the displayed panels may include presentation panels similar to presentation panels 164 and 166 of FIG. 7.

At stage 214, the selection circuitry 26 receives a selection of a medical record in presentation panel 162, which in this embodiment is a clinical note 200. The selection is provided by the user clicking the clinical note 200. In further embodiments, the user may click one or more keywords of the clinical note 200, or otherwise select at least part of the clinical note 200.

At stage 216, the highlighting circuitry 28 identifies a plurality of keywords in the clinical note 200. Each of the keywords may comprise, for example, a name of a measured parameter. Each keyword may comprise, for example, a single word, a combination of words, a phrase, or an abbreviation. In the embodiment of FIG. 9, the keywords are: IVC diameter, LDVd, and PG formulation.

The highlighting circuitry 28 highlights each of the keywords by coloring regions 150 around each of the keywords. The highlighting circuitry 28 also highlights the selected clinical note 200 using a dotted box 232.

At stage 218, the highlighting circuitry 28 generates a respective new presentation panel 180, 182, 184 for each of the identified keywords. The display circuitry 24 displays each of the new presentation panels 180, 182, 184 on display screen 16.

The generation of the new presentation panels 180, 182, 184 is represented in FIG. 9 by arrow assembly 230. Arrow assembly 230 is shown in FIG. 9 for purposes of illustration, and is not actually displayed to the user on display screen 16 in this embodiment.

Presentation panel 180 is a smaller version of presentation panel 164 of FIG. 7, and shows a plot of IVC diameter against time. The plot of presentation panel 180 includes three data points 174, 176, 178. Presentation panel 182 is a plot of left ventricular diastolic dimension (LVDd) against time, and includes four data points 190, 192, 194, 196. Presentation panel 184 is a plot of medication against time, showing one bar 170 which is representative of administration of PG formulation over time, and one point 172 which is representative of administration of Feburic tablet at a single time.

At stage 220 of FIG. 8, the highlighting circuitry 28 chooses how to display the selected clinical note's context in the newly generated presentation panels 180, 182, 184.

At stage 222, the highlighting circuitry 28 updates the presentation panels 180, 182, 184 to display the context of the selected clinical note 200. In the present embodiment, the highlighting circuitry 28 highlights point 174, point 190 and bar 170, which each relate to values for parameters referenced in the selected clinical note 200.

In some embodiments, the highlighting circuitry or other processing resource is configured to determine information from a word, sentence or other content of the clinical notes or other medical record, and the highlighting of at least one feature on the second or other presentation panel comprises highlighting or displaying said determined information or a feature derived from said determined information.

In the description above, medical data may include any form of clinical data or research data relating to any patient or other subject. Medical may include veterinary.

Aspects of the embodiments described above many be combined in any appropriate combination. For example, any appropriate combination of presentation panels may be used to display any suitable data in any appropriate data presentation. Any appropriate feature in one presentation panel may be selected, and any appropriate feature in another presentation panel or panels may be highlighted in response to the selection. The selected feature and highlighted feature may represent the same or corresponding data. The selected feature may represent at least part of a medical record, and the highlighted feature may represent a further at least part of the medical record using a different type of data presentation.

The embodiments above described hovering or clicking using a mouse. However, in alternative embodiments, any suitable input method may be used. In some embodiments, the presentation panels are displayed on a touch screen, and the selection of the feature is by touching the touch screen, for example by using a gesture on the touch screen to select the feature.

Certain embodiments provide a graphic user interface system, comprising of a collection of presentation views, which display discrete clinical record(s) in differing formats, in which: the user can indicate a clinical record item within a first view; and the system responds by updating at least one further view to indicate that record's context within the view.

The user may use a mouse event or touch gesture to indicate the clinical record item within a first view. The user may enter record identifier as text to indicate the clinical record item within a first view. The record's context may be indicated in other views by panning, zooming or scrolling the view so that the record appearance is visible. The record's context may be indicated in other views by highlighting text that references the clinical record item within the first view. The record's context may be indicated by displaying a date and time indicator on other views using a timestamp of the record on the first view.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whist certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods end systems described herein may be made without departing from the spirit of the invention. The accompanying claims and their equivalents are intended to cover such forms and modifications as would fall within the scope of the invention.

The invention claimed is:

1. A medical data presentation apparatus, comprising:
   processing circuitry; and
   at least one display device,
   wherein the processing circuitry configured to
      obtain medical data relating to a patient or other subject, the medical data comprising a plurality of medical records;
      display, on the at least one display device, at least some of the medical data on a first presentation panel of a plurality of presentation panels;
      receive, from a user, a selection of at least one feature of the first presentation panel, the at least one feature of the first presentation panel relating to a first medical record of the plurality of medical records;
      search at least one further presentation panel for a reference to the first medical record in the at least one further presentation panel; and
      in response to the selection of the at least one feature and the searching of the at least one further presentation panel, highlight at least one feature on a second presentation panel of the at least one further presentation panel in which the reference to the first medical record is found, the second presentation panel having a different type of data presentation than the first presentation panel, and the highlighted at least one feature in the second presentation panel relating to the first medical record.

2. The apparatus according to claim 1, wherein the second presentation panel displays at least some of the medical data or data derived from at least some of the medical data.

3. The apparatus according to claim 1, wherein the medical data obtained by the processing circuitry comprises clinical notes or other medical records.

4. The apparatus according to claim 3, wherein the processing circuitry is further configured to determine information from a word, sentence, or other content of the clinical notes or other medical record, and the highlighting of at least one feature on the second presentation panel comprises highlighting or displaying the determined information or a feature derived from the determined information.

5. The apparatus according to claim 1, wherein the at least one feature of the first presentation panel comprises a time or range of times, and wherein the highlighting of the at least one feature of the second presentation panel by the processing circuitry comprises indicating the time or range of times on the second presentation panel.

6. The apparatus according to claim 1, wherein the at least one feature of the first presentation panel comprises a time or range of times, and wherein the at least one feature of the second presentation panel comprises at least part of a medical record associated with at said time or range of times.

7. The apparatus according to claim 1, wherein:
the at least one feature of the first presentation panel comprises a selected time or range of times;
the medical data obtained by the processing circuitry comprises a plurality of medical records each associated with a respective time or range of times; and
the at least one feature of the second presentation panel comprises at least part of the one of the plurality of medical records for which the associated time or range of times matches or is nearest to said selected time or range of times.

8. The apparatus according to claim 1, wherein the highlighting performed by the processing circuitry comprises adjusting the second presentation panel such that the at least one feature of the second presentation panel becomes visible to the user or another user, or so that the position of the at least one feature of the second presentation panel changes relative to the second presentation panel.

9. The apparatus according to claim 8, wherein the adjusting of the second presentation panel comprises at least one of panning, zooming, and scrolling.

10. The apparatus according to claim 1, wherein the processing circuitry is further configured to highlight the at least one feature of the second presentation panel substantially without otherwise changing the second presentation panel.

11. The apparatus according to claim 1, wherein the second presentation panel is not displayed at the time of selection of the least one feature of the first presentation panel, and the processing circuitry is further configured to display the second presentation panel in response to the selection of the at least one feature of the first presentation panel.

12. The apparatus according to claim 1, wherein the processing circuitry is further configured to display, in response to the selection of the at least one feature of the first presentation panel, a message associated with the at least one feature of the first presentation panel.

13. The apparatus according to claim 1, further comprising a user input device, wherein the selection of the at least one feature is provided by the user performing an action with the user input device.

14. The apparatus according to claim 13, wherein the action comprises at least one of a hover action, a click, a dragging action, a touch action, a swipe, a gesture, a voice input, a keyboard input, a mouse input, entering a record identifier, eye tracking, and other suitable user input action.

15. The apparatus according to claim 1, wherein the at least one feature of the first presentation panel and/or the at least one feature of the second presentation panel comprises or is representative of at least one of at least one data item of the medical data, at least one numerical value, a numerical range, a scale or part of a scale, at least part of a text entry, a time, a time range, at least part of a table of results, at least part of a clinical note, and at least part of a medical record.

16. The apparatus according to claim 1, wherein the highlighting of the at least one feature in the second presentation panel by the processing circuitry comprises at least one of changing a text color, changing a background color, changing a text format, displaying an indicator, displaying an animation, animating an existing feature, and overlaying an indicator or other feature.

17. The apparatus according to claim 1, wherein at least one of:
the obtaining of the medical data comprises obtaining the medical data from a plurality of different data sources; and
the medical data comprises medical records formatted in a plurality of different data formats.

18. The apparatus according to claim 1, wherein the medical data comprises a plurality of medical records, each medical record comprising at least one of a clinical note, a set of lab results, a set of medical image data, a set of medical image measurements, a set of monitoring data, a set of patient events, medication data, and administration or records data.

19. The apparatus according to claim 1, wherein the first presentation panel comprises a first type of data presentation and the second presentation panel comprises a second type of data presentation, each of the first and second type of data presentation being one of a time line, a table of results, a list of results, a chart, a plot, a graph, a trend graph over time, a text narrative, a display of medical notes, a display of patient identifying data, and a display of imaging data.

20. The apparatus according to 18, wherein the at least one feature of the first presentation panel and the at least one feature of the second presentation panel each represent at least some of a same information displayed differently in the different types of data presentation.

21. The apparatus according to claim 1, wherein the medical data comprises medical data associated with at least one of stroke or suspected stroke, cardiology, and oncology.

22. A medical data presentation method, comprising:
obtaining medical data relating to a patient or other subject, the medical data comprising a plurality of medical records;
displaying at least some of the medical data on a first presentation panel of a plurality of presentation panels;
receiving, from a user, a selection of at least one feature of the first presentation panel or the medical data, the at least one feature of the first presentation panel relating to a first medical record of the plurality of medical records; and searching at least one further presentation panel for a reference to the first medical record in the at least one further presentation panel;

in response to the selection of the at least one feature and the searching of the at least one further presentation panel, highlighting at least one feature of a second presentation panel of the at least one further presentation panel in which the reference to the first medical record is found, the second presentation panel having a different type of data presentation than the first presentation panel, and the highlighted at least one feature in the second presentation panel relating to the first medical record.

23. A non-transitory computer-readable storage medium storing computer readable instructions that when executed, cause a computer to perform a method, comprising:

obtaining medical data relating to a patient or other subject, the medical data comprising a plurality of medical records;

displaying at least some of the medical data on a first presentation panel of a plurality of presentation panels;

receiving, from a user, a selection of at least one feature of the first presentation panel or the medical data, the at least one feature of the first presentation panel relating to a first medical record of the plurality of medical records; and searching at least one further presentation panel for a reference to the first medical record in the at least one further presentation panel;

in response to the selection of the at least one feature and the searching of the at least one further presentation panel, highlighting at least one feature of a second presentation panel of the at least one further presentation panel in which the reference to the first medical record is found, the second presentation panel having a different type of data presentation than the first presentation panel, and the highlighted at least one feature in the second presentation panel relating to the first medical record.

\* \* \* \* \*